(12) United States Patent
Ahmed

(10) Patent No.: US 7,292,153 B1
(45) Date of Patent: Nov. 6, 2007

(54) SYSTEM AND METHOD FOR DETERMINING A VEHICLE DRIVER'S BLOOD/ALCOHOL LEVEL

(76) Inventor: Omar Ahmed, 6211 W. Byron St., Chicago, IL (US) 60634

( * ) Notice: Subject to any disclaimer, the term of this patent is extended or adjusted under 35 U.S.C. 154(b) by 165 days.

(21) Appl. No.: 11/300,843

(22) Filed: Dec. 16, 2005

(51) Int. Cl.
*G08B 23/00* (2006.01)

(52) U.S. Cl. .................. 340/576; 340/573.1; 180/272; 422/84; 250/341.8

(58) Field of Classification Search ................ 340/576, 340/439, 573.1; 436/900, 901; 180/272; 422/84; 250/341.8
See application file for complete search history.

(56) References Cited

U.S. PATENT DOCUMENTS

| | | | |
|---|---|---|---|
| 4,268,751 A | 5/1981 | Fritzlen et al. | |
| D307,284 S | 4/1990 | Del Corno et al. | |
| 5,349,187 A | 9/1994 | Azzazy et al. | |
| 5,422,485 A | 6/1995 | Bowlds | |
| 6,060,989 A | 5/2000 | Gehlot | |
| 6,067,167 A | 5/2000 | Atkinson et al. | |
| 2007/0024454 A1* | 2/2007 | Singhal | 340/576 |

* cited by examiner

*Primary Examiner*—Benjamin C. Lee
*Assistant Examiner*—Travis R. Hunnings

(57) ABSTRACT

A system includes a laser beam generating device that transmits a wireless first signal, having a first monochromatic radiation level, toward the driver. The first signal bounces off the driver and returns a second signal towards the acetaldehyde level detecting mechanism. A radiation intensity level of the second signal, having a second monochromatic radiation level, is analyzed for determining the driver's blood acetaldehyde level. A mechanism is included for detecting a level of acetaldehyde in a driver's blood stream, which is located within a law enforcement vehicle. A mechanism is included for visually displaying the acetaldehyde level so that the officer can determine whether a threshold level is exceeded. The visually displaying mechanism includes a monitor including a graphical user interface. A mechanism is included for monitoring a location of the vehicle driver so that the officer can track and apprehend the driver.

12 Claims, 4 Drawing Sheets

SYSTEM AND METHOD FOR DETERMINING A VEHICLE DRIVER'S BLOOD/ALCOHOL LEVEL

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to determining systems and, more particularly, to a system and method for determining a vehicle driver's blood/alcohol level.

2. Prior Art

In the law enforcement area, it is of great value to determine the Blood Alcohol Content (BAC) of subjects suspected of driving while intoxicated where the BAC may be subsequently used as evidence in a related court proceeding. While direct blood analysis is acceptable and widely used, it is expensive and time consuming. For many years it has been known that ethanol (the specific type of alcohol of interest) appears in the breath of an individual in a direct proportion to the individual's BAC. Thus many instruments which measure a breath sample have been designed to express the test result directly in BAC using the established and legally accepted blood breath correlation factor.

Unfortunately, such instruments have many disadvantages associated therewith. One significant drawback to using breath analyzers is the fact that there is no means for determining the person's BAC prior to pulling them over, thus some persons who are intoxicated might never be pulled over. Another drawback to breath analyzing devices becomes evident when BAC checks of the general public are performed. In order to effectively do this, the officers must constrict traffic on a roadway to one lane and physically test every person, or randomly pick persons, to perform such test on. Not only is this time consuming, but the flow of traffic is greatly impeded with this practice.

There are many instances during a person's travel where their vehicle and themselves are stationary for a period of time, like when paying at a toll booth, stopping at a traffic signal or stopping at a stop sign. It would be advantageous to have a means for remotely detecting a person's BAC during periods such as these. Not only would this increase the chances of detecting an inebriated person, it would also allow for improved flow of the general traffic without causing major delays.

Accordingly, a need remains for a system and method for determining a vehicle driver's blood/alcohol level in order to overcome the above-noted shortcomings. The present invention satisfies such a need by providing a blood alcohol determining system that is automatic in operation, reliable in use and enhances the safety of traveling on roadways. Such a system pinpoints an intoxicated person to police officers, thus allowing the officers to take actions towards safely removing them from the road. The system also eliminates the need to stop all motorists at a checkpoint, in order to search for violators. Thus, the system is very appealing to law enforcement, public officials, and law-abiding citizens.

BRIEF SUMMARY OF THE INVENTION

In view of the foregoing background, it is therefore an object of the present invention to provide a system and method for determining a vehicle driver's blood/alcohol level. These and other objects, features, and advantages of the invention are provided by a system for remotely detecting a vehicle driver's blood/alcohol level while the driver is seated within the vehicle during operating conditions.

The system includes a portable laser beam generating device that is directly operated by a law enforcement officer. Such a device transmits a wireless first signal toward the driver. The first signal has a first monochromatic radiation level. Such a first signal bounces off of the driver and returns a second signal towards the acetaldehyde level detecting mechanism wherein a radiation intensity level of the second signal is analyzed for effectively determining the acetaldehyde level in the blood steam of the driver. The second signal has a second monochromatic radiation level. The first monochromatic radiation level may be greater than the second monochromatic radiation level when the acetaldehyde level is greater than the threshold level.

A mechanism is included for remotely detecting a real-time level of acetaldehyde in a blood stream of the driver. Such an acetaldehyde level detecting mechanism is located within a law enforcement vehicle and is directly operable by a law enforcement officer. The acetaldehyde level detecting mechanism is electrically coupled to an internal power supply source of the vehicle. Such an acetaldehyde level detecting mechanism preferably includes a processor and a memory that has software instructions for causing the system to determine a level of acetaldehyde in the blood stream of the driver. The software instructions have programmable operations executing the steps of calculating a molar absorbtivity of the driver's blood stream, calculating a path length of a selected body portion of the driver through which the first signal passes, calculating a concentration of acetaldehyde in the blood stream, and multiplying quantities associated with steps a, b and c to obtain a unit-less value that identifies a real-time level of acetaldehyde in the blood stream.

A mechanism is included for visually displaying the acetaldehyde level in such a manner that the law enforcement officer can advantageously quickly and accurately determine whether the acetaldehyde level has exceeded a predetermined legal threshold level. Such a threshold level preferably has a wavelength light absorption level equal to approximately 340 nanometers. The visually displaying mechanism is electrically coupled to the acetaldehyde level detecting mechanism. Such a visually displaying mechanism includes a monitor including a graphical user interface for conveniently illustrating the acetaldehyde level in a graph model.

A mechanism is included for monitoring a real-time location of the vehicle driver so that the law enforcement officer can advantageously track and apprehend the driver from a remote distance. Such a real-time location monitoring mechanism is electrically coupled to the visually displaying mechanism.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
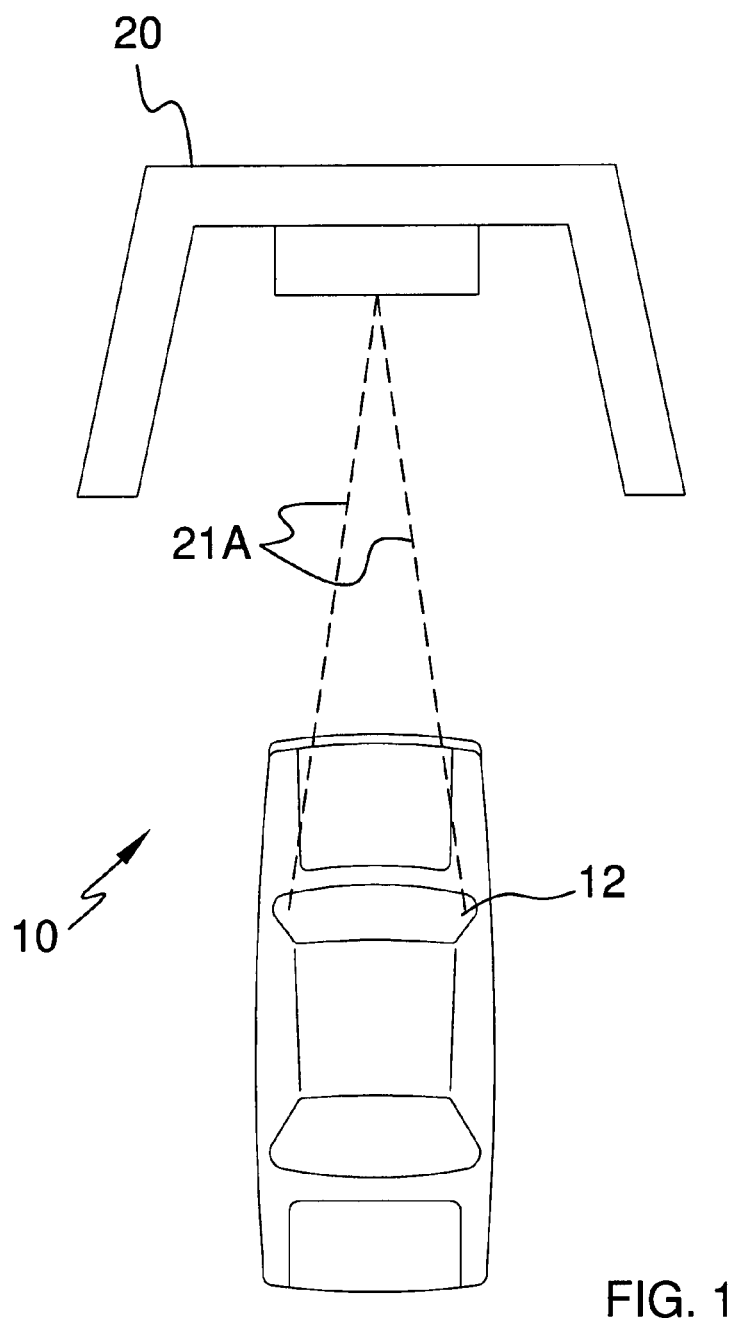
FIG. 1 is a top plan view showing a system and method for determining a vehicle driver's blood/alcohol level, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The system of this invention is referred to generally in FIGS. 1-5 by the reference numeral 10 and is intended to provide a system and method for determining a vehicle driver's blood/alcohol level. It should be understood that the system 10 may be used to detect many different types of substances in a person's bloodstream and should not be limited in use to only determining the alcohol content of a person's blood.

Figure 2:
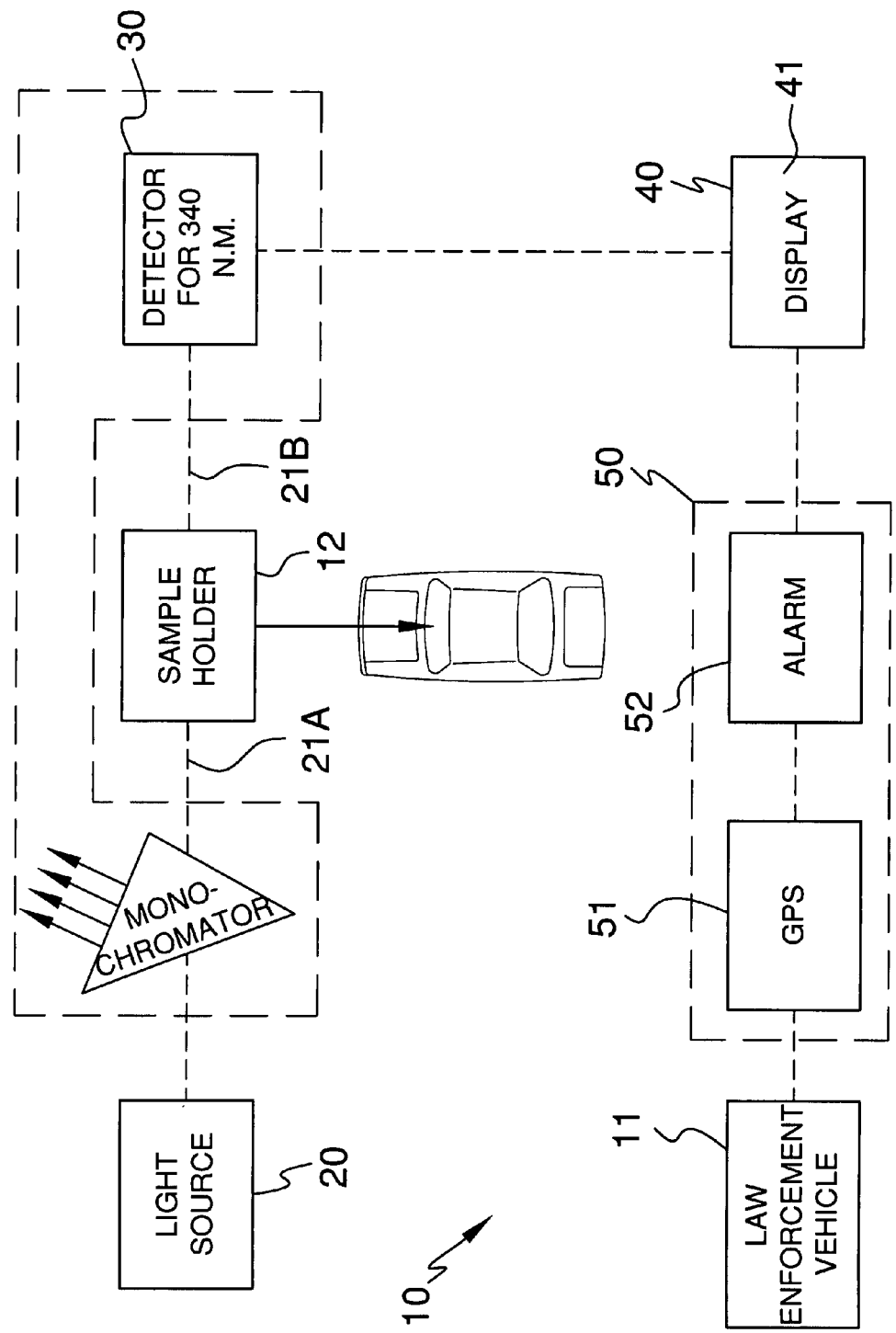
FIG. 2 is a schematic block diagram of the system shown in FIG. 1.
Figure 3:
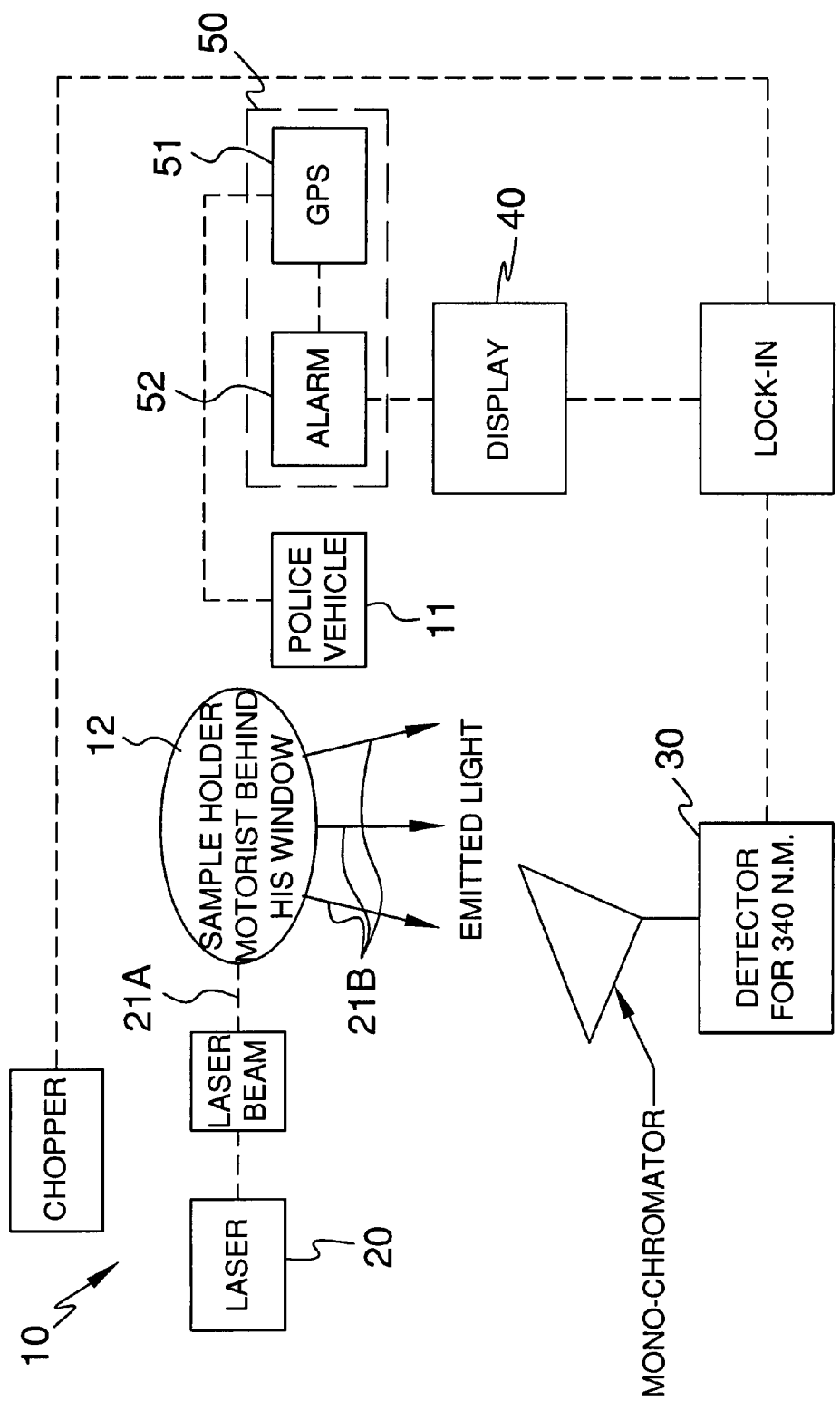
FIG. 3 is a schematic block diagram of the system shown in FIG. 1, showing a law enforcement aircraft for tracking the intoxicated motorist.

Referring initially to FIGS. 1, 2 and 3, through 3, the system 10 includes a portable laser beam generating device 20 that is directly operated by a law enforcement officer. Such a device 20 transmits a wireless first signal 21A toward the driver 12. The first signal 21A has a first monochromatic radiation level. Such a first signal 21A bounces off of the driver 12 and returns a second signal 21B towards the acetaldehyde level detecting mechanism 30 (described herein below) wherein a radiation intensity level of the second signal 21B is analyzed, which is essential for effectively determining the acetaldehyde level in the blood steam of the driver 12. The second signal 21B has a second monochromatic radiation level. The first monochromatic radiation level is greater than the second monochromatic radiation level when the acetaldehyde level is greater than the threshold level.

Referring to FIGS. 2 and 3, a mechanism 30 is included for remotely detecting a real-time level of acetaldehyde in a blood stream of the driver 12. Such an acetaldehyde level detecting mechanism 30 is located within a law enforcement vehicle 11 and is directly operable by a law enforcement officer. The acetaldehyde level detecting mechanism 30 is electrically coupled to an internal power supply source of the vehicle 11, which is advantageous for ensuring that the system 10 is always functional and convenient since the system 10 does not require a separate power supply source.

Figure 4:
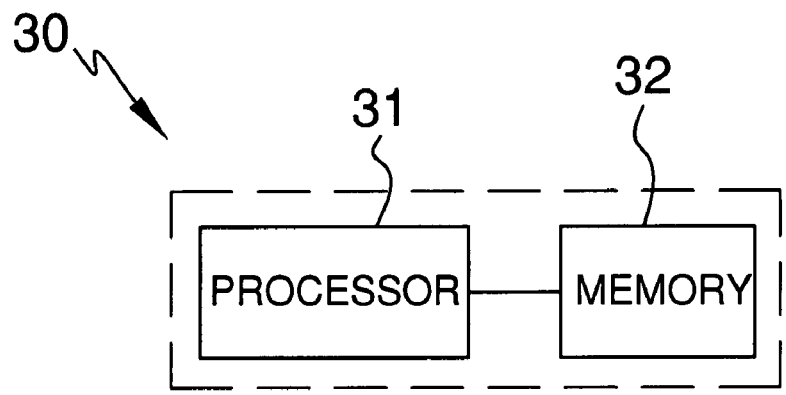
FIG. 4 is a schematic block diagram of the acetaldehyde level detecting mechanism shown in FIGS. 2 and 3.

Referring to FIG. 4, such an acetaldehyde level detecting mechanism 30 includes a processor 31 and a memory 32 that has software instructions for causing the system 10 to determine a level of acetaldehyde in the blood stream of the driver 12. The software instructions have programmable operations executing the steps of calculating a molar absorbtivity of the driver's blood stream (a) and calculating a path length of a selected body portion of the driver 12 through which the first signal 21A passes (b). Further steps include calculating a concentration of acetaldehyde in the blood stream (c) and multiplying the quantities associated with steps a, b and c to obtain a unit-less value that effectively identifies a real-time level of acetaldehyde in the blood stream. The acetaldehyde level detecting mechanism 30 works on the principle stated by the Beer-Lambert Law. According to the Beer-Lambert Law, the absorbance (A) of a substance is equivalent to the molar absorbtivity ($\epsilon$) thereof, multiplied by the path length (b) of the sample and the concentration (c) of the substance in solution. The resulting equation is as follows:

$$A = \epsilon b c$$

As such, the concentration of a substance in solution can conveniently be found by rearranging the equation to the following:

$$c = A / \epsilon b$$

Thus, it is vital for the system 10 to calculate the molar absorbtivity of the driver's blood (step a) and the path length of the selected body part (step b) in order to correctly determine the concentration of acetaldehyde in the driver's blood.

Figure 5:
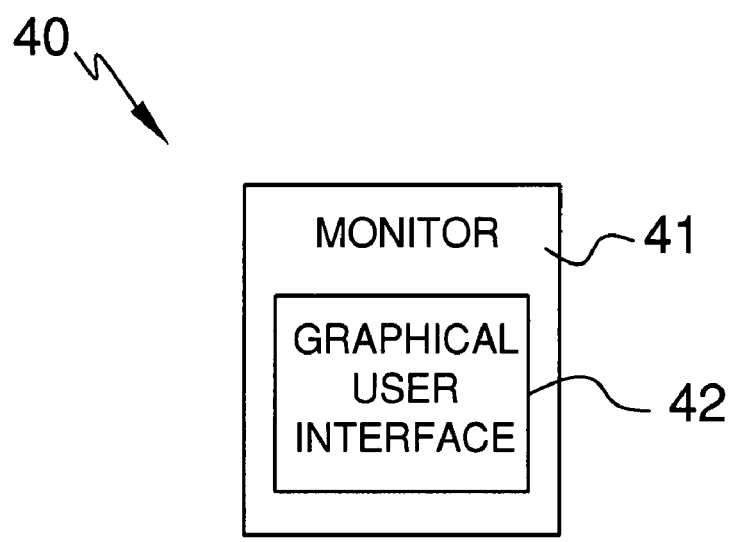
FIG. 5 is a schematic block diagram of the visually displaying mechanism shown in FIGS. 2 and 3.

Referring to FIGS. 2, 3 and 5, a mechanism 40 is included for visually displaying the acetaldehyde level in such a manner that the law enforcement officer can advantageously quickly and accurately determine whether the acetaldehyde level has exceeded a predetermined legal threshold level. Such a threshold level has a wavelength light absorption level equal to approximately 340 nanometers. The visually displaying mechanism 40 is electrically coupled to the acetaldehyde level detecting mechanism 30. Such a visually displaying mechanism 40 includes a monitor 41 including a graphical user interface 42 for conveniently illustrating the acetaldehyde level in a graph model. The graph model can quickly and easily be interpreted by the law enforcement officer to determine whether a motorist 12 is intoxicated or not.

Still referring to FIGS. 2 and 3, a mechanism 50 is included for monitoring a real-time location of the vehicle driver so that the law enforcement officer can advantageously track and apprehend the driver 12 from a remote distance. Such a real-time location monitoring mechanism 50 is electrically coupled to the visually displaying mechanism 40. The real-time location monitoring mechanism includes a GPS device 51 that is important allowing a law enforcement officer to visually detect and track a location of the intoxicated driver. An alarm 52 is electrically coupled to the GPS device 51, which is advantageous for audibly notifying an officer when a driver's blood acetaldehyde level exceeds a threshold level of acetaldehyde.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A system for remotely detecting a vehicle driver's blood/alcohol level while the driver is seated within the vehicle during operating conditions, said system comprising:

a portable laser beam generating device directly operated by a law enforcement officer;

means for remotely detecting a real-time level of acetaldehyde in a blood stream of the driver, said acetaldehyde level detecting means being located within a law enforcement vehicle and directly operable by a law enforcement officer;

means for visually displaying the acetaldehyde level in such a manner that the law enforcement officer can quickly and accurately determine whether the acetaldehyde level has exceeded a predetermined legal threshold level, said visually displaying means being electrically coupled to said acetaldehyde level detecting means; and means for monitoring a real-time location of the vehicle driver so that the law enforcement officer can track and apprehend the driver from a remote distance, said real-time location monitoring means being electrically coupled to said visually displaying means;

wherein said device transmits a wireless first signal toward the driver, said first signal having a first monochromatic radiation level, said first signal bouncing of the driver and returning a second signal towards said acetaldehyde level detecting means wherein a radiation intensity level of said second signal is analyzed for determining the acetaldehyde level in the blood steam of the driver, said second signal having a second monochromatic radiation level.

2. The system of claim 1, wherein said acetaldehyde level detecting means comprises:
   a processor;
   a memory having software instructions that cause said system to determine a level of acetaldehyde in the blood stream of the driver, said software instructions having programmable operations executing the steps of:
   a. calculating a molar absorbtivity of the driver blood stream,
   b. calculating a path length of a selected body portion of the driver through which said first signal passes,
   c. calculating a concentration of acetaldehyde in the blood stream, and
   d. multiplying quantities associated with steps a, b and c to obtain a unit-less value that identifies a real-time level of acetaldehyde in the blood stream.

3. The system of claim 1, wherein said threshold level has a wavelength light absorption level equal to approximately 340 nanometers.

4. The system of claim 1, wherein said first monochromatic radiation level is greater than said second monochromatic radiation level when said acetaldehyde level is greater than said threshold level.

5. A system for remotely detecting a vehicle driver's blood/alcohol level while the driver is seated within the vehicle during operating conditions, said system comprising:

a portable laser beam generating device directly operated by a law enforcement officer;

means for remotely detecting a real-time level of acetaldehyde in a blood stream of the driver, said acetaldehyde level detecting means being located within a law enforcement vehicle and directly operable by a law enforcement officer;

means for visually displaying the acetaldehyde level in such a manner that the law enforcement officer can quickly and accurately determine whether the acetaldehyde level has exceeded a predetermined legal threshold level, said visually displaying means being electrically coupled to said acetaldehyde level detecting means, wherein said visually displaying means comprises a monitor including a graphical user interface for illustrating the acetaldehyde level in a graph model; and means for monitoring a real-time location of the vehicle driver so that the law enforcement officer can track and apprehend the driver from a remote distance, said real-time location monitoring means being electrically coupled to said visually displaying means;

wherein said device transmits a wireless first signal toward the driver, said first signal having a first monochromatic radiation level, said first signal bouncing of the driver and returning a second signal towards said acetaldehyde level detecting means wherein a radiation intensity level of said second signal is analyzed for determining the acetaldehyde level in the blood steam of the driver, said second signal having a second monochromatic radiation level.

6. The system of claim 5, wherein said acetaldehyde level detecting means comprises:
   a processor;
   a memory having software instructions that cause said system to determine a level of acetaldehyde in the blood stream of the driver, said software instructions having programmable operations executing the steps of:
   a. calculating a molar absorbtivity of the driver blood stream,
   b. calculating a path length of a selected body portion of the driver through which said first signal passes,
   c. calculating a concentration of acetaldehyde in the blood stream, and d. multiplying quantities associated with steps a, b and c to obtain a unit-less value that identifies a real-time level of acetaldehyde in the blood stream.

7. The system of claim 5, wherein said threshold level has a wavelength light absorption level equal to approximately 340 nanometers.

8. The system of claim 5, wherein said first monochromatic radiation level is greater than said second monochromatic radiation level when said acetaldehyde level is greater than said threshold level.

9. A system for remotely detecting a vehicle driver's blood/alcohol level while the driver is seated within the vehicle during operating conditions, said system comprising:

a portable laser beam generating device directly operated by a law enforcement officer;

means for remotely detecting a real-time level of acetaldehyde in a blood stream of the driver, said acetaldehyde level detecting means being located within a law enforcement vehicle and directly operable by a law enforcement officer, wherein said acetaldehyde level detecting means is electrically coupled to an internal power supply source of the vehicle;

means for visually displaying the acetaldehyde level in such a manner that the law enforcement officer can quickly and accurately determine whether the acetaldehyde level has exceeded a predetermined legal threshold level, said visually displaying means being electrically coupled to said acetaldehyde level detecting means, wherein said visually displaying means comprises a monitor including a graphical user interface for illustrating the acetaldehyde level in a graph model; and means for monitoring a real-time location of the vehicle driver so that the law enforcement officer can track and apprehend the driver from a remote distance, said real-time location monitoring means being electrically coupled to said visually displaying means;

wherein said device transmits a wireless first signal toward the driver, said first signal having a first monochromatic radiation level, said first signal bouncing of the driver and returning a second signal towards said acetaldehyde level detecting means wherein a radiation intensity level of said second signal is analyzed for determining the acetaldehyde level in the blood steam of the driver, said second signal having a second monochromatic radiation level.

10. The system of claim 9, wherein said acetaldehyde level detecting means comprises:

a processor;

a memory having software instructions that cause said system to determine a level of acetaldehyde in the blood stream of the driver, said software instructions having programmable operations executing the steps of:

a. calculating a molar absorbtivity of the driver blood stream, b. calculating a path length of a selected body portion of the driver through which said first signal passes, c. calculating a concentration of acetaldehyde in the blood stream, and d. multiplying quantities associated with steps a, b and c to obtain a unit-less value that identifies a real-time level of acetaldehyde in the blood stream.

11. The system of claim 9, wherein said threshold level has a wavelength light absorption level equal to approximately 340 nanometers.

12. The system of claim 9, wherein said first monochromatic radiation level is greater than said second monochromatic radiation level when said acetaldehyde level is greater than said threshold level.

* * * * *